United States Patent [19]
Upmalis

[11] Patent Number: 6,153,635
[45] Date of Patent: Nov. 28, 2000

[54] METHODS AND KITS FOR TREATING VULVOVAGINAL CANDIDIASIS WITH MICONAZOLE NITRATE

[76] Inventor: David H. Upmalis, 51 Declaration Dr., Newtown, Pa. 18940

[21] Appl. No.: 09/197,019

[22] Filed: Nov. 20, 1998

[51] Int. Cl.⁷ .................................................. A61K 31/415
[52] U.S. Cl. ........................................... 514/399; 514/931
[58] Field of Search ...................................... 514/399, 931

[56] References Cited

PUBLICATIONS

Olin, B.R. et al., Facts and Comparisons, St. Louis, MO: JB Lippincott Co. (Oct. 1985) pp. 355a–355b.
Olin, B.R. et al., Facts and Comparisons, St. Louis, MO: J.B. Lippincott Co. (Nov. 1989), pp. 528–530.

Primary Examiner—Theodore J. Criares
Attorney, Agent, or Firm—Reed Smith Shaw & McClay LLP

[57] ABSTRACT

A method for treating vulvovaginal candidiasis including the steps of: (a) administering a single dose of an effective amount of miconazole nitrate in a pharmaceutically acceptable carrier intra-vaginally; and (b) applying miconazole nitrate in a pharmaceutically acceptable carrier to the vulva. Also a kit for the treatment of vulvovaginal candidiasis including: (a) a single dose of an effective amount of miconazole nitrate in a pharmaceutically acceptable carrier and in a form adapted to be administered intra-vaginally; and (b) an amount of miconazole nitrate in a pharmaceutically acceptable carrier adapted to be applied topically to the vulva.

13 Claims, No Drawings

METHODS AND KITS FOR TREATING VULVOVAGINAL CANDIDIASIS WITH MICONAZOLE NITRATE

FIELD OF THE INVENTION

The present invention relates to methods for the treatment of vulvovaginal candidiasis with miconazole nitrate and more particularly to methods for the treatment of vulvovaginal candidiasis employing a single dose of miconazole nitrate applied intra-vaginally and additional doses of miconazole nitrate applied topically to the vulva.

BACKGROUND OF THE INVENTION

Vulvovaginal candidiasis is a relatively common form of yeast infection. Treatment of vulvovaginal candidiasis with the anti-fungal composition miconazole nitrate is well known. The most common regimen of treatment of vulvovaginal candidiasis with miconazole nitrate comprises the intra-vaginal application of a cream or other pharmaceutically acceptable carrier containing miconazole nitrate once a day for 1, 3 or 7 days depending upon the concentration of miconazole nitrate in the cream. Thus, commercial kits for the treatment of vulvovaginal candidiasis with miconazole nitrate comprise a supply of vaginal suppositories or cream containing miconazole nitrate and a suitable applicator for administering the miconazole nitrate intra-vaginally.

While these methods of treating vulvovaginal candidiasis are highly effective, there is a certain amount of discomfort and inconvenience for the patient in having to repeatedly administer the miconazole nitrate intra-vaginally. Both of these disadvantages can affect patient compliance and, therefore, the effectiveness of the treatment. In addition, relief of symptoms can take 4–5 days or more.

Accordingly, there is a need for improved methods for treating vulvovaginal candidiasis with miconazole nitrate that are more convenient and comfortable than known methods and that provide faster relief of vulvovaginal candidiasis.

SUMMARY OF THE INVENTION

The present invention is directed to a method for treating vulvovaginal candidiasis consisting essentially of the steps of: (a) administering a single dose of an effective amount of miconazole nitrate in a pharmaceutically acceptable carrier intra-vaginally; and (b) applying miconazole nitrate in a pharmaceutically acceptable carrier to the vulva.

The present invention is also directed to a kit for the treatment of vulvovaginal candidiasis comprising: (a) a single dose of an effective amount of miconazole nitrate in a pharmaceutically acceptable carrier and in a form adapted to be administered intra-vaginally; and (b) an amount of miconazole nitrate in a pharmaceutically acceptable carrier adapted to be applied topically to the vulva.

DETAILED DESCRIPTION OF THE PREFERRED EMBODIMENT(S)

It has been discovered that the intra-vaginal administration of a single dose of miconazole nitrate in combination with the topical administration of a miconazole nitrate cream to the vulva is at least as effective as previously known treatment regimens comprising 3 to 7 daily intra-vaginal doses of miconazole nitrate and results in faster relief of vulvovaginal candidiasis symptoms. In particular, studies comparing the effectiveness of standard 7 day miconazole nitrate intra-vaginal treatment regimens to treatment regimens comprising a single intra-vaginal dose of miconazole nitrate in combination with a miconazole nitrate cream applied topically to the vulva found that the single dose miconazole nitrate intra-vaginal treatment in combination with a topical miconazole nitrate cream resulted in faster therapeutic cure rates and equivalent microbiological and clinical cure rates. Similar comparisons of 3 day to 7 day therapies have not shown such an effect.

Methods for treating vulvovaginal candidiasis with miconazole nitrate in accordance with the present invention comprise the steps of: (a) administering a single dose of an effective amount of miconazole nitrate in a pharmaceutically acceptable carrier intra-vaginally; and (b) applying miconazole nitrate in a pharmaceutically acceptable carrier to the vulva as needed.

The dose of miconazole nitrate in a pharmaceutically acceptable carrier administered intra-vaginally may be in the form of a gelatin capsule, a cream, or any other intra-vaginal delivery system. The intra-vaginal dose of miconazole nitrate preferably comprises from about 400–2000 mg of miconazole nitrate, more preferably from about 600–1200 mg of miconazole nitrate. Delivery systems and phamaceutically acceptable carriers for intra-vaginally delivered miconazole nitrate are known to those of ordinary skill in the art.

The dose of miconazole nitrate applied to topically to the vulva may be a cream or other pharmaceutically acceptable carrier containing from about 1% to 4% mg miconazole nitrate in a form adapted to be applied topically. A preferred topical cream comprising 2% miconazole nitrate is marketed by Advanced Care Products, Personal Products Co. as MONISTAT® EXTERNAL VULVAR CREAM. It is believed that in addition to the synergistic effect of the combining the single intra-vaginal miconazole nitrate dose with the topical doses applied to the vulva, the topical doses provide for immediate temporary relief of vulvovaginal candidiasis symptoms. Accordingly, the dose of miconazole nitrate applied to the vulva is preferably applied 1–2 times daily as needed for up to about 7 days for the immediate temporary relief of vulvovaginal candidiasis symptoms.

The invention will be clarified further by a consideration of the following Examples, which are intended to be purely exemplary.

EXAMPLES

As used herein, "clinical cure" means that no symptoms of vulvovaginal candidiasis were detected upon physical examination. "Microbiological cure" means that a culture for candidiasis was negative. "Therapeutic cure" means that no additional treatment was indicated for vulvovaginal candidiasis

Example 1

A study was performed comparing results of treatment of vulvovaginal candidiasis with: (1) a single dose of 1200 mg of miconazole nitrate in a gelatin capsule in an ointment base administered intra-vaginally in combination with MONISTAT® EXTERNAL VULVAR CREAM (with instructions to apply as necessary, up to twice daily, for symptomatic relief); versus (2) MONISTAT®[7] Vaginal Cream.

The study population was as follows. 278 patients with vulvovaginal candidiasis were entered. 266 (96%) of the patients were valid for safety. 213 (77%) of the patients were valid for efficacy at return visit 1. 196 (71%) of the patients were valid for overall efficacy. About 60% of the patients were white, with most of the remaining patients either hispanic or black. Mean age of the patients was 33–34 years. Just over one third of the patients reported oral contraceptive use. Disease severity was mild or moderate in over 90% of the patients. 4–7% of the patients reported severe disease. The two treatment groups appeared comparable at baseline.

Results of treatment in Example I are set forth in Tables 1 and 2.

TABLE 1

|  | GROUP 1: Miconazole Nitrate (1200 mg) Vaginal Ovule & MONISTAT ® External Vulvar Cream (N = 99) | | GROUP 2: MONISTAT ® 7 Vaginal Cream (N = 97) | |
| --- | --- | --- | --- | --- |
| Overall Cure Rate | n | % | n | % |
| Clinical | 81 | 81.8 | 79 | 81.4 |
| Microbiological | 75 | 75.8 | 71 | 73.2 |
| Therapeutic | 71 | 71.7 | 68 | 70.1 |

TABLE 2

|  | GROUP 1: Miconazole Nitrate (1200 mg) Vaginal Ovule & MONISTAT ® External Vulvar Cream | | GROUP 2: MONISTAT ® 7 Vaginal Cream | |
| --- | --- | --- | --- | --- |
| Relief at 3 days | 29/94 | (30.9%) | 15/92 | (16.3%) |
| Relief at 7 days | 66/94 | (70.2%) | 64/92 | (69.6%) |

Overall clinical, microbiological and therapeutic cure rates were almost identical in the two treatment groups. There was no statistically significant difference in the overall therapeutic cure rates (p=0.96). The 95% confidence intervals for the difference in overall cure rates, clinical cure rates (−10.5%, 11.2%), microbiological cure rates (−9.7%, 14.8%) and therapeutic cure rates (−11.1%, 14.3%) indicate that the two formulations are therapeutically equivalent. However, relief of itching and burning/irritation was significantly higher in Group 1 at Day 3 (p=0.025). Median time to symptom relief was four days in Group 1 and five days in Group 2.

Example 2

A study identical in design to that reported in Example 1 was performed on a second population. In Example 2, the study population was as follows. 280 patients with vulvovaginal candidiasis were entered. 271 (97%) of the patients were valid for safety. 205 (73%) of the patients were valid for efficacy at return visit 1. 194 (69%) of the patients were valid for overall efficacy. Somewhat fewer Group 2 patients were evaluable at both return visit 1 and overall because of more screening failures in this group. About 70% of patients were white, with most of the remaining patients either black or hispanic. Mean age of the patients was 36.3 years. About 20–25% of the patients reported oral contraceptive use. Disease severity was mild or moderate in over 95% of the patients. 2% of the patients reported severe disease. The two treatment groups appeared comparable at baseline.

Results of treatment in Example 2 are set forth in Tables 3 and 4.

TABLE 3

|  | GROUP 1: Miconazole Nitrate (1200 mg) Vaginal Ovule & MONISTAT ® External Vulvar Cream (N = 104) | | GROUP 2: MONISTAT ® 7 Vaginal Cream (N = 90) | |
| --- | --- | --- | --- | --- |
| Overall Cure Rate | n | % | n | % |
| Clinical | 72 | 69.2 | 63 | 70.0 |
| Microbiological | 72 | 69.2 | 62 | 68.9 |
| Therapeutic | 64 | 61.5 | 55 | 61.1 |

TABLE 4

|  | GROUP 1: Miconazole Nitrate (1200 mg) Vaginal Ovule & MONISTAT ® External Vulvar Cream | | GROUP 2: MONISTAT ® 7 Vaginal Cream | |
| --- | --- | --- | --- | --- |
| Relief at 3 days | 41/100 | (41.0%) | 19/85 | (22.4%) |
| Relief at 7 days | 66/100 | (66.0%) | 59/85 | (69.4%) |

Overall clinical, microbiological and therapeutic cure rates were almost identical in the two treatment groups. There was no statistically significant difference in the overall therapeutic cure rates (p=0.775). The 95% confidence intervals for the difference in overall cure rates, clinical cure rates (−13.7, 12.2), microbiological cure rates (−12.7, 13.4) and therapeutic cure rates (−13.3, 14.2) indicate that the two formulations are therapeutically equivalent. However, relief of itching and burning/irritation was significantly higher in Group 1 at day 3 (p=0.008). Median time to symptom relief was three days in Group 1 and four days in Group 2.

Example 3

A dose-ranging study was performed comparing: (1) various doses of miconazole nitrate in one-dose cream formulations in combination with MONISTAT® EXTERNAL VULVAR CREAM (with instructions to apply as necessary, up to twice daily, for symptomatic relief); against (2) MONISTAT® 7 Vaginal Cream.

Patients were randomized equally to one of the following five regimens:

Group 1: a single intra-vaginal dose of 2.5 grams of 16% miconazole nitrate vaginal cream containing 400 mg of miconazole nitrate in combination with MONISTAT® EXTERNAL VULVAR CREAM (with instructions to apply as necessary, up to twice daily, for symptomatic relief);

Group 2: a single intra-vaginal dose of 5 grams of 8% miconazole nitrate vaginal cream containing 400 mg of miconazole nitrate in combination with MONISTAT® EXTERNAL VULVAR CREAM (with instructions to apply as necessary, up to twice daily, for symptomatic relief);

Group 3: a single intra-vaginal dose of 5 grams of 12% miconazole nitrate vaginal cream containing 600 mg of miconazole nitrate in combination with MONISTAT® EXTERNAL VULVAR CREAM (with instructions to apply as necessary, up to twice daily, for symptomatic relief);

Group 4: a single intra-vaginal dose of 5 grams of 16% miconazole nitrate vaginal cream containing 800 mg of miconazole nitrate in combination with MONISTAT® EXTERNAL VULVAR CREAM (with instructions to apply as necessary, up to twice daily, for symptomatic relief); and Group 5: 7 daily doses of MONISTAT® 7 (2% miconazole nitrate) Vaginal Cream each containing 100 mg per dose of miconazole nitrate.

The study population was as follows. 230 patients with vulvovaginal candidiasis were entered. 228 (99%) of the patients were valid for safety. 186 (81%) of the patients were valid for efficacy. Mean ages of the patients by treatment groups were 34.5 years to 38.3 years. 59.1% to 72.9% of the patients were white, with most remaining patients classified as black or hispanic. Oral contraceptive use by treatment group ranged from 15.9% to 34.1%. Disease severity was mild or moderate in over 90% of the patients with severe disease reported in from 2.3% to 9.1% of the patients by treatment group. Despite some differences, the five treatment groups were reasonably comparable at baseline.

Results of treatment in Example 3 are set forth in Tables 5 and 6.

TABLE 5

| Study Group | Clinical Cure n | % | Microbiological Cure n | % | Therapeutic Cure n | % |
|---|---|---|---|---|---|---|
| Group 1 | 32/36 | 88/9 | 27/36 | 75.0 | 25/36 | 69.4 |
| Group 2 | 36/37 | 97.3 | 27/37 | 73.0 | 27/37 | 73.0 |
| Group 3 | 39/42 | 92/9 | 36/42 | 85.7 | 34/42 | 81.0 |
| Group 4 | 35/38 | 92.1 | 35/38 | 92.1 | 32/38 | 84.2 |
| Group 5 | 29/33 | 87.9 | 27/33 | 81.8 | 26/33 | 78.8 |

TABLE 6

| Study Group | Symptomatic Relief at Day 3 n | % | Symptomatic Relief at Day 7 n | % |
|---|---|---|---|---|
| Group 1 | 7/34 | 21 | 22/34 | 65 |
| Group 2 | 16/31 | 52 | 25/31 | 81 |
| Group 3 | 13/39 | 33 | 31/39 | 79 |
| Group 4 | 10/38 | 26 | 33/38 | 87 |
| Group 5 | 4/29 | 14 | 20/29 | 69 |

Clinical, microbiological and therapeutic cure rates were acceptable for all five treatment regimens. Microbiological and therapeutic cure rates were highest in Groups 3 and 4. Proportions of patients obtaining symptomatic relief at 3 and 7 days varied widely, with the highest rates at both time intervals in Groups 2–4. Median time to relief of symptoms was also quite variable: 3 days in Group 2; 4 days in Groups 1 and 3; and 5 days in Groups 4 and 5. While statistical analysis was not performed on the Day 3 cure rates due to the smallness of the sample size, it appears that the cure rates on Day 3 are higher for Groups 1–4 (single intra-vaginal dose plus topical cream regimens) than Group 5 (7-day/dose intra-vaginal regimen).

Example 4

A study was performed comparing: (1) a regimen of MONISTAT® 3 Suppositories (200 mg miconazole nitrate) plus MONISTAT® EXTERNAL VULVAR CREAM (with instructions to apply as necessary, up to twice daily, for symptomatic relief); against (2) a regimen of MONISTAT® 7 Vaginal Cream (5-grams, 100 mg miconazole nitrate) plus MONISTAT® EXTERNAL VULVAR CREAM (with instructions to apply as necessary, up to twice daily, for symptomatic relief).

The study population was as follows. 263 patients were enrolled. 257 (98%) of the patients were valid for safety. 195 (74%) of the patients were valid for efficacy at return visit 1. 183 (70%) of the patients were valid for overall efficacy. Just over 60% of the patients were caucasian, and approximately 29% of the patients were black. Women on MONISTAT®3 were about two years older than women on MONISTAT®7 (36.3 vs. 34.7 years). Oral contraceptive use was less frequent on MONISTAT®3 (23% vs. 34%). More patients on MONISTAT®7 admitted to intercourse and did not always use a condom between admission and return visit 1, and also between return visits 1 and 2. Disease severity was mild or moderate in over 90% of the patients at baseline. The two groups appeared reasonably comparable overall.

Results of treatment in Example 4 are set forth in Table 7.

TABLE 7

| Days to Relief in Patients Valid for Overall Efficacy | | |
|---|---|---|
| | Group 1: MONISTAT ® 3 Vaginal Suppositories & MONISTAT ® External Vulvar Cream | Group 2: MONISTAT ® 7 Vaginal Cream & MONISTAT ® External Vulvar Cream |
| Day 3 | 32/91 (35%) | 20/90 (22%) |
| Day 7 | 63/91 (69%) | 58/90 (64%) |

Overall clinical, microbiological and therapeutic cure rates were comparable in the two treatment groups. Cure rates were also comparable in patients valid for efficacy at return visit 1. The difference between Groups 1 and 2 in symptomatic relief at day 3 was not statistically significant.

It will be understood by person by persons skilled in the art that various changes in the details, components, steps, and arrangements of the components and steps which have been described and illustrated in order to explain the nature of this invention may be made by those skilled in the art without departing from the principle and scope of the invention as expressed in the following claims.

What is claimed is:

1. A method for treating vulvovaginal candidiasis consisting essentially of the steps of:
    (a) administering a single dose of an effective amount of miconazole nitrate in a pharmaceutically acceptable carrier intra-vaginally; and
    (b) applying topically miconazole nitrate in a pharmaceutically acceptable carrier to the vulva.

2. The method of claim 1, wherein the single dose of miconazole nitrate administered intra-vaginally comprises about 400 to about 2000 mg of miconazole nitrate.

3. The method of claim 1, wherein the single dose of miconazole nitrate administered intra-vaginally comprises about 600 to about 1200 mg of miconazole nitrate.

4. The method of claim 1, wherein the single dose of miconazole nitrate administered intra-vaginally comprises 2.5 g of 16% miconazole nitrate cream, 5 g of 8% miconazole nitrate cream, 5 g 12% miconazole nitrate cream or 5 g 16% miconazole nitrate cream.

5. The method of claim 1, wherein step (b) is performed 1–2 times per day.

6. The method of claim 1, wherein step (b) is performed 1–2 times per day for about 7 days.

7. The method of claim 3, wherein step (b) is performed 1–2 times per day for about 7 days.

8. A kit for the treatment of vulvovaginal candidiasis consisting essentially of:
   (a) a single dose of an effective amount of miconazole nitrate in a pharmaceutically acceptable carrier and in a form adapted to be administered intra-vaginally; and
   (b) an amount of miconazole nitrate in a pharmaceutically acceptable carrier adapted to be applied topically to the vulva.

9. The kit of claim 8, wherein the single dose of miconazole nitrate adapted to be administered intra-vaginally comprises about 400 to about 2000 mg of miconazole nitrate.

10. The kit of claim 8, wherein the single dose of miconazole nitrate adapted to be administered intra-vaginally comprises about 600 to about 1200 mg of miconazole nitrate.

11. The kit of claim 8, wherein the single dose of miconazole nitrate adapted to be administered intra-vaginally comprises 2.5 g of 16% miconazole nitrate cream, 5 g of 8% miconazole nitrate cream, 5 g 12% miconazole nitrate cream or 5 g 16% miconazole nitrate cream.

12. The kit of claim 8, wherein the amount of miconazole nitrate in a pharmaceutically acceptable carrier adapted to be applied topically to the vulva is a sufficient amount to be applied 1–2 times per day for about 7 days.

13. The kit of claim 10, wherein the amount of miconazole nitrate in a pharmaceutically acceptable carrier adapted to be applied topically to the vulva is a sufficient amount to be applied 1–2 times per day for about 7 days.

* * * * *